(12) United States Patent
Faour et al.

(10) Patent No.: US 6,605,302 B2
(45) Date of Patent: Aug. 12, 2003

(54) DRUG DELIVERY DEVICE CONTAINING OSELTAMIVIR AND AN H1 ANTAGONIST

(75) Inventors: Joaquina Faour, Buenos Aires (AR); Juan A. Vergez, Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/907,486

(22) Filed: Jul. 17, 2001

(65) Prior Publication Data

US 2003/0044457 A1 Mar. 6, 2003

(51) Int. Cl.[7] .............................. A61K 9/20; A61K 9/22; A61K 9/24; A61K 9/44; A61K 9/52

(52) U.S. Cl. .................... 424/473; 4243/457; 4243/458; 4243/464; 4243/468; 4243/472; 4243/474

(58) Field of Search ................................ 424/464, 468, 424/451, 457, 473, 472, 458, 474, 489, 471

(56) References Cited

U.S. PATENT DOCUMENTS

| 5,240,694 A | 8/1993 | Gwaltney, Jr. |
| 5,422,097 A | 6/1995 | Gwaltney, Jr. |
| 5,492,689 A | 2/1996 | Gwaltney, Jr. |
| 5,658,581 A | 8/1997 | De Lacharriere et al. |
| 5,756,486 A | 5/1998 | Alexander et al. |
| 5,763,483 A | 6/1998 | Bischofberger et al. |
| 5,866,601 A | 2/1999 | Lew et al. |

*Primary Examiner*—James M. Spear
(74) *Attorney, Agent, or Firm*—Rick Matos; Innovar, L.L.C.

(57) ABSTRACT

The present invention provides a dual release solid dosage form containing a first composition that releases oseltamivir in a controlled manner and a second composition that releases an H1 antagonist in a rapid and/or immediate manner. A wide range of H1 antagonist antihistamines, especially fexofenadine and loratadine, can be used in this device. Particular embodiments of the invention provide osmotic devices having predetermined release profiles. The device is useful for the treatment of respiratory congestion and other viral infection associated symptoms.

38 Claims, 2 Drawing Sheets

DRUG DELIVERY DEVICE CONTAINING OSELTAMIVIR AND AN H1 ANTAGONIST

FIELD OF THE INVENTION

Figure 1:
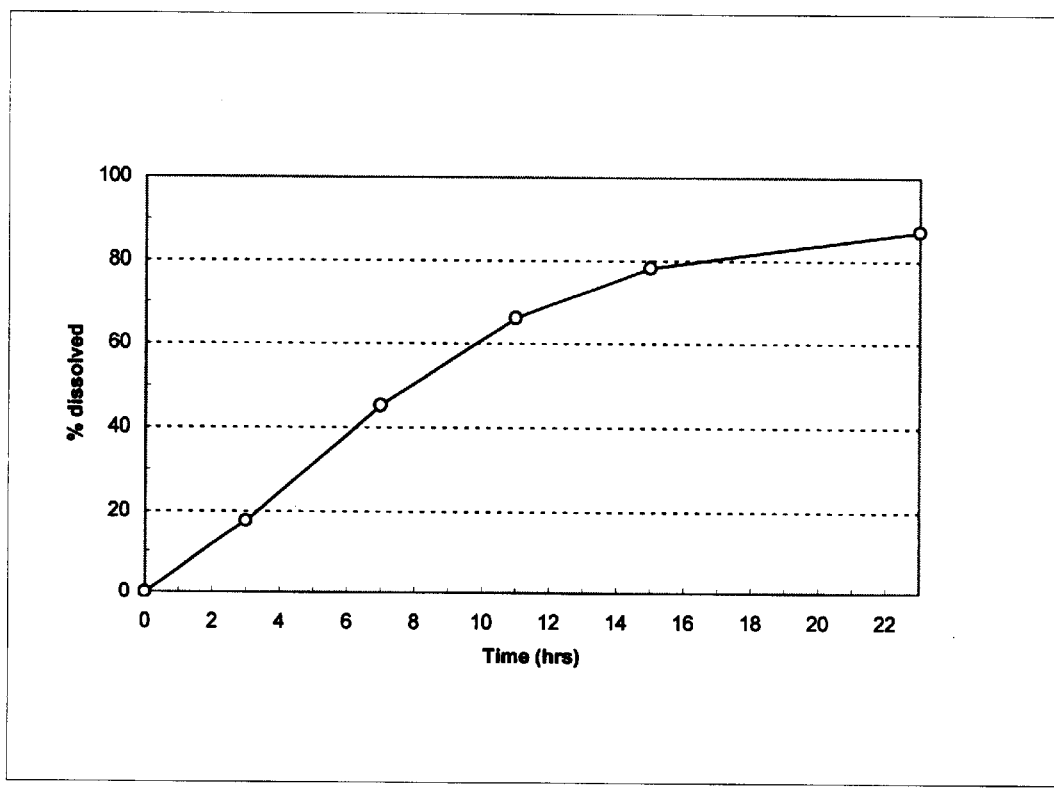

This invention pertains to a solid oral dosage form containing an antiviral agent and an H1 antagonist, or antihistamine. More particularly, it pertains to dual release osmotic device tablet, which provides a controlled (sustained) release of oseltamivir and a rapid (or immediate) release of an H1 antagonist.

BACKGROUND OF THE INVENTION

Antihistamines, such as H1 histamine receptor antagonists (herein referred to as "H1 antagonists" or "antihistamines"), are used to treat seasonal allergic rhinitis (SAR) and can be used to treat nasal congestion, e.g., stuffed or blocked nasal passages. Epidemiological, biological and clinical studies have shown that viral respiratory infections before the age of 3 years play a crucial role in the later development of rhinitis and asthma. Reduction of their frequency and severity may effect the viral alteration of the pulmonary and immune systems.

A new class of specific anti-influenza agents, the neuraminidase inhibitors, has demonstrated potent inhibition of both influenza A and B viruses. Oseltamivir (OS, GS4104, EN 241104, RO 64-0796, oseltamivir phosphate, an antiviral neuraminidase inhibitor) is used for the treatment of viral infections; however, it does not treat nasal congestion. Oseltamivir is the ethyl ester prodrug of the carbocyclic transition state sialic acid analog RO 64-0802 (GS4071), a potent and selective inhibitor of influenza A and B virus neuraminidases. Oral oseltamivir was approved for treatment of acute influenza in the United States in 1999. It has demonstrated efficacy both in treating and preventing influenza illness.

For antiviral agents to be effective, they must be used within 48 hours of the onset of influenza symptoms. Antiviral agents reduce the duration of fever and illness by one to two and one-half days and also reduce the severity of some symptoms. Although, oseltamivir reduces the severity of some symptoms, it does not reduce nasal congestion or the production of excessive mucous in the respiratory tract to the same degree that an H1 histamine receptor antagonist does. Consequently, nasal congestion or the production of excessive mucous in the respiratory tract lingers in patients having been administered oseltamivir.

G. He et al. (*Clin. Pharmacokinet.* (December 1999), 37(6), pp. 471–484) report that oral administration of oseltamivir delivers the active antiviral RO 64-0802 to the bloodstream, and thus all sites of influenza infection (lung, nasal mucosa, middle ear) are accessible. They report that the pharmacokinetic profile of oseltamivir is simple and predictable, and that twice-daily treatment results in effective antiviral plasma concetrations over the entire administration interval. After oral administration, oseltamivir is readily absorbed from the gastrointestinal tract and extensively converted to the active metabolite. The absolute bioavailability of the active metabolite from orally administered oseltamivir is reportedly about 80%. The active metabolite is detectable in plasma within 30 minutes and reaches maximal concentrations after 3 to 4 hours with the dosage form used in that study. After peak plasma concentrations are attained, the concentration of the active metabolite declines with an apparent half-life of 6 to 10 hours. Oseltamivir is eliminated primarily by conversion to and renal excretion of the active metabolite. The pharmacokinetic profile of the active metabolite is reportedly linear and dose-proportional, with less than 2-fold accumulation over a dosage range of oseltamivir 50 to 500 mg twice daily. Steady-state plasma concentrations are achieved within 3 days of twice daily administration with the dosage form used in that study. At a dosage of 75 mg twice daily, the steady-state plasma trough concentrations of active metabolite remain above the minimum inhibitory concentration for all influenza strains tested. Exposure to the active metabolite at steady state is approximately 25% higher in elderly compared with young individuals; however, no dosage adjustment is necessary. In patients with renal impairment, metabolite clearance decreases linearly with creatinine clearance. A dosage reduction to 75 mg once daily is recommended for patients with creatinine clearance <30 ml/min (1.8 L/h). The pharmacokinetics in patients with influenza are reportedly qualitatively similar to those in healthy young adults.

J. Gwaltney (U.S. Pat. No. 5,240,694, No. 5,492,689, and No. 5,422,097 discloses COVAM (combined virostatic antimediator) therapy, which includes a method and compositions for the treatment of the common cold. The method requires the nasal administration of an antiviral composition, optionally containing an antihistamine, and the concurrent oral administration of at least one anti-inflammatory agent. Gwaltney does not disclose a method or composition for the effective treatment of the common cold or other viral infections wherein both the antiviral agent and the antihistamine agent are administered orally. Moreover, Gwaltney does not disclose or suggest a dual release oral solid dosage form containing oseltamivir and an H1 antagonist.

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770, U.S. Pat. No. 4,008,719 to Theeuwes et al., U.S. Pat. No. 4,058,122 to Theeuwes et al., U.S. Pat. No. 4,116,241 to Theeuwes et al., U.S. Pat. No. 4,160,452 to Theeuwes, U.S. Pat. No. 4,256,108 to Theeuwes, and Argentina Patent No. 199,301, the entire disclosures of which are hereby incorporated by reference. In particular, tablet formulations for providing antihistamines are disclosed in U.S. Pat. No. 4,650,807 to Findlay et al., and U.S. Pat. No. 4,501,893 to Findlay et al., the entire disclosures of which are hereby incorporated by reference.

Dual release conventional sustained release dosage forms are known for the concurrent or sequential administration of two or more drugs by a single unit dosage form. To date, none of the art discloses a dual release oral dosage form that provides a controlled release of an antiviral agent and a rapid release of an H1 antihistamine, or a controlled or sustained release of oseltamivir and a rapid or immediate release of an H1 antihistamine.

While conventional sustained release dosage forms, such as described above, are effective, osmotic devices such as those described by Faour et al. (U.S. Pat. No. 6,004,582), the entire disclosure of which is hereby incorporated by reference, are particularly advantageous for delivering two different dosage forms from a single osmotic device tablet. Faour et al., however, do not disclose osmotic device formulations comprising slow release oseltamivir combined with a rapid release H1 antagonist. They also do not disclose osmotic devices that provide the specific formulations, plasma profiles or release profiles for the various different combinations claimed herein.

SUMMARY OF THE INVENTION

In one aspect, the present invention provides a dual release drug delivery system comprising:

- a first composition comprising a therapeutically effective amount of oseltamivir (OS) and at least one pharmaceutical excipient; and
- a different second composition comprising a therapeutically effective amount of an H1 histamine receptor antagonist;
- wherein the first composition provides a controlled or sustained release of oseltamivir and the second composition provides a rapid or immediate release of an H1 histamine receptor antagonist.

Specific embodiments of the invention include those wherein: 1) the drug delivery system is selected from the group consisting of capsules containing immediate and sustained release granules, capsules containing sustained release granules and one or more immediate release tablets, capsules containing sustained release granules and powder, and extended release film or multi-layer coated tablets; 2) at least 75% of the H1 antagonist is released within about 120 minutes and at least about 70% of the oseltamivir is released within about 24 hours; 3) the first drug composition comprises at least one release rate modifier; 4) the second drug composition comprises an H1 histamine receptor antagonist and at least one pharmaceutical excipient; 5) the first and second drug compositions are in layered arrangement with respect to one another; 6) the second drug composition surrounds the first drug composition; 7) the first drug composition is included in a core and the second drug composition is included in a coat, of one or more coats, surrounding the core; 8) the drug delivery device is a capsule containing the first and second compositions, the first composition is a granulation, and the second composition is a powder, granulation or compressed tablet.

One embodiment of the invention provides an osmotic device comprising:

- a core comprising a therapeutically effective amount of oseltamivir (OS) and at least one osmotic agent or osmopolymer, wherein the core provides a controlled release of OS;
- a semipermeable membrane surrounding the core and having a passageway there through; and
- a drug-containing coat comprising a therapeutically effective amount of an H1 antagonist and surrounding the semipermeable membrane, wherein the external coat provides a rapid release of the H1 antagonist.

Specific embodiments of the osmotic device include those wherein: 1) the osmotic device further comprises an inert water soluble coat interposed the semipermeable membrane and the drug-containing coat; 2) the osmotic device further comprises one or more other coats surrounding the core, wherein the coats are selected from the group consisting of: inert water soluble or water erodible coat, and immediate, rapid, or delayed release coat; 3) the OS is released in a controlled or sustained manner over a period of about 20–24 hours after exposure to an aqueous environment; 4) the H1 antihistamine is released over a period of about 5–120, or 15–120, or 5–60 minutes after exposure to an aqueous environment; 5) osmotic device has an OS dissolution profile and an H1 antagonist dissolution profile as described herein.

In some embodiments, the H1 antagonist is selected from the group consisting of acrivastine, astemizol, azelastine, cetirizine, ebastine, epinastine, fexofenadine, loratadine, mizolastine, norastemizol, prometazine and terfenadine.

In other embodiments, the external coat is applied by spray coating rather than by compression coating. By spray coating rather than compression coating the external coat is thinner, and therefore a smaller osmotic device is formed.

Another aspect of the invention provides a method of treating the symptoms of or of ameliorating a viral infection or a common cold. The method comprises the step of administering a dual release dosage form comprising OS and an H1 antagonist, wherein the OS is released in a sustained manner and the H1 is released rapidly.

Target therapeutic levels for the H1 antagonist are in the range of about 2 ng to about 700 ng per ml of plasma.

Target therapeutic levels for the OS are generally in the range of about 30 to about 200 ng per ml of plasma and, for the active metabolite, in the range of about 250 to about 1300 ng/ml.

Other features, advantages and embodiments of the invention will become apparent to those skilled in the art by the following description, accompanying examples.

BRIEF DESCRIPTION OF THE DRAWINGS

The following drawings are part of the present specification and are included to further demonstrate certain aspects of the invention. The invention may be better understood by reference to one or more of these drawings in combination with the detailed description of the specific embodiments presented herein.

FIG. 1 depicts a dissolution profile for oseltamivir as it is released in a controlled manner from a dosage form according to Example 1.

FIG. 2 depicts a dissolution profile for fexofenadine as it is released from a dosage form according to Example 1.

DETAILED DESCRIPTION OF THE INVENTION

Oseltamivir phosphate (Ro64-0796, GS4104) is a prodrug of oseltamivir carboxylate (Ro64-0802, GS4071), a potent and selective inhibitor of the neuraminidase glycoprotein essential for replication of influenza A and B viruses. Oseltamivir (Tamiflu®) is available from Roche Pharma™ AG (Switzerland). Alternatively, oseltamivir can be prepared according to the methods described in U.S. Pat. No. 5,763,483 to Bischofberger et al and U.S. Pat. No. 5,866,601 to Lew et al., the disclosures of which are hereby incorporated by reference.

H1 antagonist antihistamines are available from large number of commercial sources. The invention provides for the administration of oseltamivir and H1 antagonists in their free base, free acid, racemic, optically pure, diastereomeric and/or pharmaceutically acceptable salt forms. Suitable H1 antagonist antihistamines include, for example, first generation antihistamines, second generation antihistamines, diphenhydramine, chlorpheniramine, brompheniramine, tripolidine, promethacine, hydroxizine, pinlamine, dimenhydrinate, acrivastine, azelastine, cetirizine, ebastine, epinastine, fexofenadine, loratadine, mizolastine, norastemizol and prometazine. These drugs are available commercially from a number of pharmaceutical manufacturers.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the OS or H1 antagonist. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences,* 18th Ed. (Alfonso R. Gennaro, ed.; Mack Publishing Company, Easton, Pa., 1990); *Remington: the Science and Practice of Pharmacy* 19th Ed. (Lippincott, Williams & Wilkins, 1995); *Handbook of Pharmaceutical Excipients,* 3rd Ed. (Arthur H. Kibbe, ed.; Amer. Pharmaceutical Assoc., 1999); the *Pharmaceutical Codex: Principles and Practice of Pharmaceutics* 12th Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

FIG. 1 depicts an OS in vitro dissolution profile for the tablets described in Example 1. The releae profile of the dual release formulation of the invention will vary from that shown in FIG. 1 according to the materials used to form the core and the semipermeable membrane covering the core.

When the formulation is an osmotic device, for example, the release profile can be influenced by the material used to form the semipermeable membrane covering the core, by the material used to form any coating on the semipermeable membrane, by the excipients present in the core, or by the presence of an osmagent in the core. The osmotic device of the invention can have a release profile that generally resembles a pseudo-second order, a second order, a pseudo-third order, or a third order release profile.

Depending upon the particular combination of ingredients used to prepare the osmotic device, the osmotic device will generally provide an expected overall OS release profile resembling a zero order, pseudo-zero order or first order profile. The dissolution profile for oseltamivir for the formulation of Example 1 is generally described as follows:

| Time (h) | Maximum released (%) | Minimum released (%) |
|---|---|---|
| 3 | 30 | 5 |
| 7 | 64 | 27 |
| 11 | 84 | 48 |
| 15 | 95 | 62 |
| 23 | 100 | 74 |

The OS dissolution profile can also be described as follows:

| Time (h) | Average (%) |
|---|---|
| 3 | 17.5 |
| 7 | 45.5 |
| 11 | 66 |
| 15 | 78.5 |
| 23 | 87 |

All of the tablet formulations of the invention will provide therapeutically effective levels of OS and an H1 antagonist for at least a predetermined period of time. The tablets of the invention will generally provide therapeutically effective amounts of OS for a period of not less than 12 hours and not more than 24 hours, or not less than 10 hours and not more than 32 hours. The controlled release core generally begins to release OS within about 0.5–2.0 hours after exposure of the osmotic device to an aqueous solution.

Figure 2:
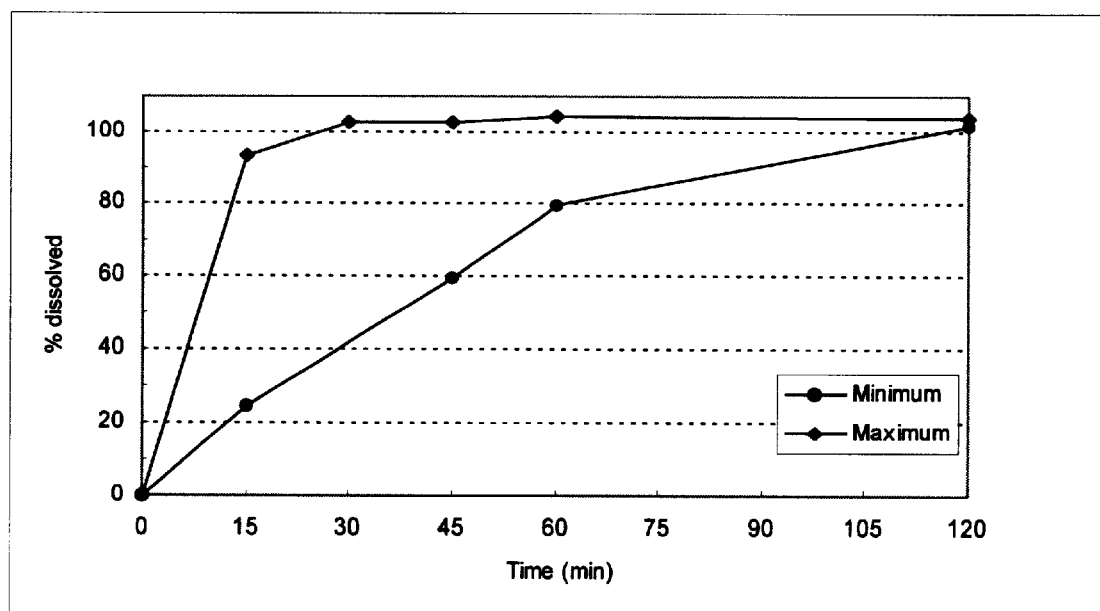

The formulation of Example 1 provides an H1 antagonist (fexofenadine) dissolution profile as depicted in FIG. 2 and an OS dissolution profile as depicted in FIG. 1. The external coating can be an immediately dissolving coating that dissolves in the buccal cavity or a rapidly dissolving coating that dissolves in the buccal cavity, stomach, jejunum or duodenum.

The dissolution profile of the H-1 antagonist is generally described as follows and depicted in FIG. 2.

| Time (min) | Minimum Released (%) | Maximum Released (%) |
|---|---|---|
| 15 | 24 | 94 |
| 30 | 40 | 100 |
| 45 | 60 | 100 |
| 60 | 80 | 100 |
| 120 | <100 | 100 |

The rapid release coating will release all of the H1 antagonist within 2 hours after administration and at least 10% of the H1 antagonist within about 10–20 minutes after administration.

Pharmacokinetic data was obtained for the formulation of Example 1, which includes oseltamivir phosphate (150 mg strength) and fexofenadine hydrochloride (120 mg strength). The following table summarizes the pharmacokinetic data.

| Active Agent | $T_{max}$ (h) | $AUC_{0-inf}$ (ng.h/ml) | $T_{1/2}$ (h) |
|---|---|---|---|
| Oseltamivir | 3 | 150–300 | 5–7 |
| Active metabolite of oseltamivir | 8 | 2500–7500 | 14 |
| Fexofenadine | 1.12–4.0 | 1716–3306 | 230–534 |

The observed $C_{max}$ for fexofenadine was about 230–534 ng/ml.

Those of ordinary skill in the art will appreciate that the particular amounts of OS and H1 antagonist used in the osmotic device will vary according to, among other things, the desired pharmacokinetic behavior in a subject.

A water-soluble coating, inert or drug-containing, will generally comprise an inert and non-toxic material which is at least partially, and optionally substantially completely, soluble or erodible in an environment of use. Selection of materials suitable for the inert or drug-containing water soluble coatings will depend upon the desired release rate of drug from the drug-containing coating and upon the desired separation of drug delivery from the core versus the drug-containing coating. A rapidly dissolving coat will be soluble in the buccal cavity and/or upper GI tract, such as the stomach, duodenum, jejunum or upper small intestines. Exemplary materials are disclosed in U.S. Pat. No. 4,576,604 to Guittard et al. and U.S. Pat. No. 4,673,405 to Guittard et al., and U.S. Pat. No. 6,004,582 to Faour et al. and the text *Pharmaceutical Dosage Forms: Tablets Volume I, 2$^{nd}$ Edition*. (A. Lieberman. ed. 1989, Marcel Dekker, Inc.), the relevant disclosures of which are hereby incorporated by reference. In some embodiments, the rapidly dissolving coat will be soluble in saliva, gastric juices, or acidic fluids.

Materials which are suitable for making the water soluble or erodible coatings of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film forming polymers.

Other materials which can be used in the water soluble or erodible coatings include hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the water soluble coat.

The inert water soluble or water erodible coat covering the semipermeable wall and blocking the passageway is made of synthetic or natural material which, through selective dissolution or erosion shall allow the passageway to be unblocked thus allowing the process of osmotic delivery to start. This slow or fast dissolving water soluble coat can be impermeable to a first external fluid, while being soluble in a second external fluid. This property can help to achieve a controlled and selective release of the active compound in the nucleus.

In some embodiments, the inert water soluble or erodible coat will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the water soluble coat. Such other polymeric materials include, by way of example and without limitation, cellulose acetate phthalate (CAP), cellulose acetate trimelletate (CAT), poly(vinyl acetate)phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit™ L-30-D (MA-EA, 1:1), Eudragit™ L-100-55 (MA-EA, 1:1), hydroxypropylmethylcellulose acetate succinate (HPMCAS), Coateric™ (PVAP), Aquateric™ (CAP), AQOAT™ (HPMCAS) and combinations thereof. The water soluble coat can also comprise dissolution aids, stability modifiers, and bioabsorption enhancers.

An optional polymeric material for use in the inert water soluble or erodible coat includes enteric materials that resist the action of gastric fluid avoiding permeation through the semipermeable wall while one or more of the materials in the core are solubilized in the intestinal tract thereby allowing delivery of a drug in the core by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The water soluble coat can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon™ K 30 has a viscosity of about 5.5–8.5 cps at 20.degree. C., and a 2% P/V aqueous solution of Methocel™ E-15 has a viscosity of about 13–18 cps at 20.degree. C.

The inert water soluble or water erodible coat can also comprise other suitable materials which are substantially resistant to gastric juices and which will promote either enteric or colonic release. For this purpose, the inert water soluble coat can comprise one or more materials that do not dissolve, disintegrate, or change their structure in the stomach and during the period of time that the osmotic device resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials that form a semipermeable wall which are known by those of ordinary skill in the art of pharmaceutical sciences are suitable for this purpose. Exemplary materials are cellulose esters, cellulose ethers and cellulose esters-ethers. However, it has been found that a semipermeable membrane comprising cellulose acetate (CA) and poly(ethylene glycol) (PEG), in particular PEG 400, performs well when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50-1% by weight of PEG, and about 95% by weight of CA: about 5% by weight of PEG. The ratio can be varied to alter permeability and ultimately the release profile of the osmotic device. Other suitable materials can include a selected member of the group of cellulose acylates such as cellulose acetate, cellulose diacetate, cellulose triacetate and combinations thereof. Many suitable polymers, include those disclosed in Argentine Patent No. 199,301, U.S. Pat. No. 6,004,582 and references cited herein, the disclosures of which are hereby incorporated by reference.

Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%; a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. No. 3,173,876, No. 3,276,586, No. 3,541,005, No. 3,541,006, and No. 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride), semipermeable polymers exhibiting a fluid permeability of $10.\text{sup.}-5$ to $10.\text{-sup.}-1$ (cc.mil/cm.sup.2.hr.atm) expressed as per atmosphere of hydrostatic or osmotic pressure difference across the semipermeable wall. These and others polymers are disclosed in U.S. Pat. No. 3,845,770, No. 3,916,899, No. 4,765,989 and No. 4,160,020; and in *Handbook of Common Polymers* (Scott, J. R. and Roff, W. J., eds.; 1971; CRC Press, Cleveland, Ohio).

The osmotic device of the invention comprises at least one passageway (pore, hole, or aperture) that communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

The core of the tablet of the present invention will comprise OS, at least one pharmaceutically acceptable excipient and optionally one or more other materials.

Generally, the tablet formulations will comprise about 0.1–99.9% by weight of OS in the uncoated tablet core. Acceptable ranges may vary according to the desired therapeutic response, the tablet size, the amount and type of excipients used in the core of the device, the H1 antagonist used and the intended use of the osmotic device.

When the controlled release tablet is an osmotic device, osmotically effective solutes, osmotic agents or osmagents are added. These osmagents can aid in either the suspension or dissolution of the OS in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of OS therefrom. U.S. Pat. No. 4,077,407 to Theeuwes et al., the entire disclosure of which is hereby incorporated by reference, discloses suitable osmagents.

The tablets of the invention can also comprise adsorbents, acidifying agent, alkalizing agent, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants, complexing agent, preservative and/or tablet polishing agents.

As used herein, a complexing agent is an agent that complexes metal ions. Exemplary complexing agents include EDTA disodium, edetate, pentates and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

As used herein, a preservative is an agent or combination of agents that inhibits, reduces or eliminates bacterial growth in a pharmaceutical dosage form. Exemplary preservatives includes Nipagin, Nipasol, Isopropyl alcohol and a combination thereof.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide, talc and other materials known to one of ordinary skill in the art.

As used herein, the term "tablet polishing agent" is intended to mean a compound used to impart an attractive sheen to coated tablets. Such compounds include, by way of example and without limitation, carnauba wax, white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth; crospovidone and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of OS, or H1 antagonist, which is sufficient to elicit the required or desired therapeutic response, or in other words, the amount which is sufficient to elicit an appreciable biological response when administered to a patient.

The tablets of the invention can assume any shape or form known in the art of pharmaceutical sciences. The device of the invention can be a pill, sphere, tablet, bar, plate, paraboloid of revolution, ellipsoid of revolution or the like. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, OS and excipients that comprise the core are mixed in solid, semisolid or gelatinous form, then moistened and sieved through a specified screen to obtain granules. The granules are then dried in a dryer and compressed, for example, by punching to form uncoated cores. The compressed and uncoated cores are then covered with a semipermeable membrane. Subsequently, the semipermeable membrane surrounding the core should be perforated with, for example, laser equipment. Finally, an external coat containing the H1 antagonist is applied to the semipermeable membrane.

The external coat can be applied as a compression coating, but it is generally applied as a sprayed coating. The sprayed coating is thinner and lighter than the compression coating, and an osmotic device including the sprayed on external coating is, therefore, smaller than a similar osmotic device having a compression coat. Moreover, the use of a sprayed-on drug-containing water soluble coating permits the loading of higher amounts of drug than the use of a compression-coated drug-containing water soluble coating.

A smaller size osmotic device generally results in increased patient compliance in taking the osmotic device and is therefore advantageous.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The method of ameliorating a viral infection or of eliminating and/or reducing severity of congestion or mucous-related symptoms associated with a viral infection comprises the step of administering a solid oral dosage form comprising oseltamivir and an H1 antagonist to a patient, wherein the OS is provided at a controlled rate for an extended period of time and the H1 antagonist is provided rapidly, i.e., within a short period of time, after administration. The method includes the steps of providing therapeutically effective levels of both drugs. This combination treatment method will reduce the severity of congestion related symptoms associated with a viral infection (such as influenza or the common cold) more so than treatment with oseltamivir alone.

The advantages of the present system over known systems for administering oseltamivir in combination with an H1 antagonist is improved therapeutic benefit, control of or amelioration of the symptoms associated with viral infection, simplified manufacturing, and/or increased patient compliance.

As used herein, the terms "controlled", "extended", "retarded" or "sustained" release are generally used interchangeably and indicate a release profile wherein the active agent is released slowly and about continually over a lengthened period of time. The intended period of time is as described herein.

The following examples should not be considered exhaustive, but merely illustrative of only a few of the many embodiments contemplated by the present invention. The methods described herein can be followed to prepare dosage forms according to the invention.

EXAMPLE 1

The following general method was used to prepare osmotic devices according to the invention. In one embodiment, a large scale batch of oseltamivir phosphate (150 mg strength, OS-Ph) and fexofenadine hydrochloride (120 mg strength) osmotic device tablets was prepared by mixing 197.00 g of OS-Ph, 145.00 g of mannitol (osmagent), and 40.00 g of povidone (binder). The mixture was wetted with a blend of 46.00 ml of alcohol 96°, 2.30 g of PEG 400 (plasticizer) and 10.00 g of PEG 6000. The blend was granulated and dried at 40–50° C. for 4 hours; then, it was screened and mixed with 2.00 g of colloidal silicon dioxide (glidant). The blend was mixed to homogeneity and 3.70 g of magnesium stearate (lubricant) was added. The final blend was tabletted using biconcave, 10.00-mm diameter punches to form uncoated cores. Core weight: 400.0 mg; hardness from 8 to 12 kp.

A first composition to cover the uncoated cores was prepared as follows: 32.30 g of cellulose acetate (cellulose ester) and 1.7 g of PEG 400 (plasticizer) was added to 1310.0 ml of a blend of acetone (710 ml) and methanol (300 ml) organic solvents. This polymer mixture was sprayed onto the tablets in a conventional pan coater to obtain film-coated tablets which membrane coating weighed approximately 34.0 mg. A 0.50-mm hole was laser drilled through the coating in one face of the tablet.

The second coating was prepared by mixing 1.95 g of copolyvidone (water soluble polymer), 1.75 g of titanium dioxide (opaquant), 6.25 g of talc and 50.00 mg of Aluminum Lake Ponceau Red (colorant) in Isopropyl Alcohol. This polymer mixture was sprayed onto the tablets in a conventional pan coater to obtain film-coated tablets which membrane coating weighed approximately 10 mg.

The third coating was prepared by mixing 120.00 g of fexofenadine hydrochloride, 150.0 g of microcrystalline cellulose (disintegrant), 100.0 g of lactose monohydrate, 35.00 g of corn starch, 32.00 g of povidone (film forming polymer). The mixture was wetted and mixed with 130.00 ml of purified water, 9.00 g of PEG 400 (plasticizer), and 30.00 g of PEG 6000. The blend was granulated and dried at 40–50° C. for 3 hours. The granulation was then sieved and mixed with 1.00 g of colloidal silicon dioxide (glidant). This blend was mixed to homogeneity and 6.00 g of magnesium stearate was mixed in as well. The final blend was compressed about the second coating using 14.00 mm diameter punches to form tablets weighing about 483.0 mg having a hardness of about 7–12 kP.

The final coating was prepared by mixing 12.10 g of HPMC 2910 (film forming polymer), 3.42 g of PEG 6000 (plasticizer) and 4.48 g of titanium dioxide (opaquant) in a mixture of methylene chloride and alcohol (96°) (70:30, v/v). This polymer mixture was sprayed onto the drug-containing third coating in a conventional pan coater to form an outer coating weighing about 20 mg.

The osmagent, diluent, binder, plasticizer, glidant, disintegrant, lubricant, cellulose ester, water soluble polymer, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

EXAMPLE 2

The following general method was used to prepare osmotic devices according to the invention. In one embodiment, a large scale batch of oseltamivir phosphate (150 mg strength, OS-Ph) and loratadine (10 mg strength) osmotic device tablets was prepared by mixing 197.00 g of OS-Ph, 55.00 g of sodium chloride (osmagent), and 40.00 g of povidone (binder). The mixture was wetted with a blend of 46.00 ml of alcohol 96°, 2.30 g of PEG 400 (plasticizer) and 10.00 g of PEG 6000. The blend was granulated and dried at 40–50° C. for 4 hours; then, it was screened and mixed with 2.00 g of colloidal silicon dioxide (glidant). The blend was mixed to homogeneity and 3.70 g of magnesium stearate (lubricant) was added. The final blend was tabletted using biconcaves, 10.00-mm diameter punches to form uncoated cores. Core weight: 310.0 mg; hardness from 8 to 12 kp.

A first composition to cover the uncoated cores was prepared as follows: 32.30 g of cellulose acetate (cellulose ester) and 1.7 g of PEG 400 (plasticizer) was added to 1310.0 ml of a blend of acetone (710 ml) and methanol (300 ml) organic solvents. This polymer mixture was sprayed onto the tablets in a conventional pan coater to obtain film-coated tablets which membrane coating weighed approximately 28.0 mg. A 0.50-mm hole was laser drilled through the coating in one face of the tablet.

The second coating was prepared by mixing 1.95 g of copolyvidone (water soluble polymer), 1.75 g of titanium dioxide (opaquant), 6.25 g of talc and 50.00 mg of Aluminum Lake Ponceau Red (colorant) in Isopropyl Alcohol. This polymer mixture was sprayed onto the tablets in a conventional pan coater to obtain film-coated tablets which membrane coating weighed approximately 12 mg.

The third coating was prepared by mixing 10.00 g of loratadine, 23.40 g of HPMC 2910 (film-forming polymer), 5.40 g of PEG 6000 (plasticizer), 9.60 g of crospovidone (binder), and 0.60 g of colloidal silicon dioxide (glidant) in purified water. This polymer mixture was sprayed onto the tablets in a conventional pan coater to obtain film-coated tablets which coating weighed approximately 49.0 mg.

The final coating was prepared by mixing 12.10 g of HPMC 2910 (film forming polymer), 3.42 g of PEG 6000 (plasticizer) and 4.48 g of titanium dioxide (opaquant) in a mixture of methylene chloride and alcohol (96°) (70:30, v/v). This polymer mixture was sprayed onto the drug-containing third coating in a conventional pan coater to form an outer coating weighing about 15 mg.

The osmagent, diluent, binder, plasticizer, glidant, lubricant, cellulose ester, water soluble polymer (disintegrant), opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

EXAMPLE 3

The following procedure was used to prepare capsules consisting essentially of oseltamivir-containing sustained release granules and loratadine-containing immediate release tablets. The capsules made according to this procedure included the following ingredients in the approximate amounts indicated.

| Ingredient | Amount (mg) |
| --- | --- |
| Oseltamivir Phosphate | 150.00 |
| Loratadine | 10.00 |
| Ethylcellulose Aqueous Dispersion | 15.00 |
| Acetylated Monoglyceride | 8.40 |
| Sodium Croscarmellose | 11.25 |
| Glyceryl Monostearate (Myvaplex 600 P) | 105.00 |
| Microcrystalline Cellulose PH 301 | 81.00 |
| Magnesium Stearate | 2.00 |
| Dicalcium Phosphate | 25.75 |
| Purified Water | 5.00 ml |

The capsules were made as follows. Oseltamivir Phosphate and Myvaplex 600 P were thoroughly mixed and melt extruded through a USP 12-mesh screen. The extrudate was spheronized and sieved through a USP 12-mesh screen. The spheronized granules were coated with an aqueous dispersion of ethylcellulose containing acetylated monoglyceride (plasticizer).

Dicalcium phosphate, loratadine, and microcrystalline cellulose PH301 were placed in a mixer and mixed for six minutes. Magnesium stearate was added to the mixture and the mixture was sieved through a USP 60-mesh screen to form a composition that was compressed into tablets having an approximate weight of about 130 milligrams each.

Size 000 capsules were filled with a loratadine-containing tablet and the desired quantity of oseltamivir granules as required to form the required dose.

EXAMPLE 4

The following procedure was used to prepare capsules consisting essentially of oseltamivir-containing sustained release granules and fexofenadine-containing immediate release capsules. The capsules made according to this procedure included the following ingredients in the approximate amounts indicated.

| Ingredient | Amount (mg) |
| --- | --- |
| Oseltamivir Phosphate | 150.00 |
| Fexofenadine | 120.00 |
| Ethylcellulose Aqueous Dispersion | 15.00 |
| Acetylated Monoglyceride | 8.40 |
| Glyceryl Monostearate (Myvaplex 600 P) | 105.00 |
| Microcrystalline Cellulose PH 101 | 51.00 |
| Gelatin | 3.00 |
| Yellow Lake N°10 D&C | 5.60 |
| Magnesium Stearate | 2.00 |
| Purified Water | 5.00 ml |

The capsules were made as follows. Oseltamivir Phosphate and Myvaplex 600 P were thoroughly mixed and melt extruded through a USP 12-mesh screen. The extrudate was spheronized and sieved through a USP 12-mesh screen. The spheronized granules were coated with an aqueous dispersion of ethylcellulose containing acetylated monoglyceride (plasticizer).

Fexofenadine and microcrystalline cellulose PH101 were placed in a mixer and mixed for six minutes and granulated with a solution of gelatin in water containing the colorant. The mass was extruded through a USP 12-mesh screen and spheronized. The extrudate was tray dried.

The oseltamivir-containing granules were mixed with the fexofenadine-containing granules at the desired ratio. Magnesium stearate was mixed with the mixture of granules to form a drug-containing composition that was filled into size 000 capsules as required to form the required dose.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. An dual release drug delivery device comprising:
   a first composition comprising a therapeutically effective amount of oseltamivir (OS) and at least one pharmaceutical excipient; and
   a different second composition comprising a therapeutically effective amount of an H1 histamine receptor antagonist;
   wherein the first composition provides a controlled, extended and/or sustained release of oseltamivir and the second composition provides a rapid and/or immediate release of an H1 histamine receptor antagonist.

2. The device of claim 1, wherein the device is selected from the group consisting of capsules containing immediate and sustained release granules, capsules containing sustained release granules and one or more immediate release tablets, capsules containing sustained release granules and powder, extended release film or multi-layer coated tablets.

3. The device of claim 2, wherein at least 75% of the H1 antagonist is released within about 120 minutes and at least about 70% of the oseltamivir is released within about 24 hours after exposure of the device to an aqueous environment.

4. The device of claim 2, wherein the first drug composition further comprises at least one release rate modifier.

5. The device of claim 2, wherein the second drug composition further comprises at least one pharmaceutical excipient.

6. The device of claim 2, wherein the first and second drug compositions are in layered arrangement with respect to one another.

7. The device of claim 2, wherein the second drug composition surrounds the first drug composition.

8. The device of claim 6 or 7, wherein the first drug composition is in contact with the second drug composition.

9. The device of claim 6 or 7, wherein the first drug composition is spaced-away from the second drug composition.

10. The device of claim 6 or 7, wherein the first drug composition is included in a core and the second drug composition is included in a coat, of one or more coats, surrounding the core.

11. The device of claim 1, wherein the first drug composition is a granulation, the second drug composition is a powder, granulation or compressed tablet and the device is a capsule.

12. An osmotic device comprising:
   a core comprising a therapeutically effective amount of oseltamivir (OS) and at least one osmotic agent or osmopolymer, wherein the core provides a controlled release of OS;
   a semipermeable membrane surrounding the core and having a passageway there through; and
   a drug-containing coat comprising a therapeutically effective amount of an H1 antagonist and surrounding the semipermeable membrane, wherein the external coat provides a rapid release of the H1 antagonist.

13. The osmotic device of claim 12, wherein the osmotic device further comprises an inert water soluble coat interposed the semipermeable membrane and the drug-containing coat.

14. The osmotic device of claim 13, wherein the drug-containing water soluble coat is sprayed onto the inert water soluble coating.

15. The osmotic device of claim 12, wherein the osmotic device further comprises one or more other coats surrounding the core.

16. The osmotic device of claim 15, wherein the one or more coats are selected from the group consisting of inert water-soluble coat, inert water-erodible coat, immediate release coat, rapid release coat, and delayed release coat.

17. The osmotic device of claim 12, wherein the OS is released in a controlled or sustained manner over a period of about 20–24 hours after exposure to an aqueous environment, and the H1 antihistamine is released over a period of about 15–120 minutes after exposure to an aqueous environment.

18. The osmotic device of claim 17, wherein 70–100% of the OS is released within 23 hours after exposure to an aqueous environment.

19. The osmotic device of claim 12, wherein the H1 antagonist is selected from the group consisting of acrivastine, astemizol, azelastine, cetirizine, ebastine, epinastine, fexofenadine, loratadine, mizolastine, norastemizol, prometazine and terfenadine.

20. The osmotic device of claim 17, wherein the device provides an oseltamivir dissolution profile approximately as follows when exposed to an aqueous environment:

| Time (h) | Maximum released (%) | Minimum released (%) |
|---|---|---|
| 3 | 30 | 5 |
| 7 | 64 | 27 |
| 11 | 84 | 48 |
| 15 | 95 | 62 |
| 23 | 100 | 74 |

21. The osmotic device of claim 20, wherein the device provides an H1 antagonist dissolution profile approximately as follows when exposed to an aqueous environment:

| Time (min) | Minimum Released (%) | Maximum Released (%) |
|---|---|---|
| 15 | 24 | 94 |
| 30 | 40 | 100 |
| 45 | 60 | 100 |
| 60 | 80 | 100 |
| 120 | 100 | |

22. An osmotic device comprising:
(a) a core comprising a therapeutically effective amount of oseltamivir (OS) which is delivered at a controlled rate over a period of at least about 18–24 hours;
(b) a semipermeable membrane surrounding the core and a passageway through the semipermeable membrane;
(c) an inert water soluble coating surrounding the semipermeable membrane and plugging the passageway; and
(d) an H1 antagonist-containing water soluble coating surrounding the inert water soluble coating for delivering all of the H1 antagonist at a rapid rate over a period of less than about 120 min.

23. The osmotic device of claim 22, wherein about 75–150 mg of OS and about 2.5–180 mg of H1 antagonist are present.

24. The osmotic device of claim 22, wherein:
the core further comprises an osmagent, a diluent and a binder;
the semipermeable membrane comprises a cellulose ester and a plasticizer;
the inert water soluble coating comprises a water soluble polymer, an opaquant and a filler; and
the H1 antagonist-containing water soluble coating further comprises a film forming polymer and a disintegrant.

25. The osmotic device of claim 24, wherein:
the osmagent is selected from the group consisting of sodium chloride, salt, mannitol, acid, sugar, base, calcium salt, sodium salt, and lactose;
the diluent is selected from the group consisting of microcrystalline cellulose, lactose, sucrose, mannitol, cellulose, starch, sorbitol, dibasic calcium phosphate, and calcium carbonate;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose ester is selected from the group consisting of cellulose acetate, cellulose acylate, cellulose fatty acid ester, and cellulose acetate phthalate;
the plasticizer is independently selected at each occurrence from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate;
the water soluble polymer is independently selected at each occurrence from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum;
the opaquant is selected from the group consisting of titanium dioxide and talc;
the filler is selected from the group consisting of talc and starch;
the film forming polymer is selected from the group consisting of hydroxypropyl methylcellulose, and poly(vinylpyrrolidone); and
the disintegrant is selected from the group consisting of crospovidone, bentonite clay, microcrystalline cellulose, starch, carboxymethylcellulose, alginate, sodium starch glycolate, and gum.

26. The osmotic device of claim 25, wherein:
the opaquant is selected from the group consisting of titanium dioxide and talc; and
the filler is selected from the group consisting of talc and starch.

27. The osmotic device of claim 24, wherein:
the osmagent is present in an amount ranging from 45–155 mg;
the diluent is present in an amount ranging from 0–100 mg;
the binder is present in an amount ranging from 20–60 mg;
the cellulose ester is present in an amount ranging from 20–50 mg;
the film-forming polymer in the H1 antagonist-containing water soluble coating is present in an amount ranging from 20–40 mg; and
the disintegrant in the H1 antagonist-containing water soluble coating is present in an amount ranging from 100–200 mg.

28. A method of treating a viral infection and reducing the respiratory congestion associated therewith comprising the step of administering a dual release drug delivery device according to any one of claims 1–7, or 11.

29. A method of treating a viral infection and reducing the respiratory congestion associated therewith comprising the step of administering an osmotic device according to any one of claims 12–21.

30. A method of treating a viral infection and reducing the respiratory congestion associated therewith comprising the step of administering an osmotic device according to any one of claims 22–25, or 27.

31. A dual release capsule comprising:
- a first composition consisting essentially of plural granules comprising a therapeutically effective amount of oseltamivir (OS) and at least one pharmaceutical excipient; and
- a different second composition comprising a therapeutically effective amount of an H1 histamine receptor antagonist;
- wherein the first composition provides a controlled or sustained release of oseltamivir and the second composition provides a rapid release of an H1 histamine receptor antagonist.

32. The capsule of claim 31, wherein the first composition is a granulation and the second composition is a powder, granulation or one or more tablets.

33. The capsule of claim 32, wherein the H1 antagonist is selected from the group consisting of acrivastine, astemizol, azelastine, cetirizine, ebastine, epinastine, fexofenadine, loratadine, mizolastine, norastemizol, prometazine and terfenadine.

34. A method of treating a viral infection and reducing the respiratory congestion associated therewith comprising the step of administering a capsule according to any one of claims 31–33.

35. A method of treating a viral infection and reducing the respitory congestion associated therewith comprising the step of administering a dual release drug delivery device comprising:
- a therapeutically effective amount of oseltamivir; and
- a therapeutically effective amount of an H1 antagonist;
- wherein the drug delivery device is administered on a once or twice daily basis; provides a controlled, sustained, retarded or extended release of the oseltamivir; and provides an immediate and/or rapid release of the H1 antagonist.

36. The method of claim 35, wherein the H1 antagonist is selected from the group consisting of acrivastine, astemizol, azelastine, cetirizine, ebastine, epinastine, fexofenadine, loratadine, mizolastine, norastemizol, prometazine and terfenadine.

37. The method of claim 35, wherein the initial release of the oseltamivir and/or H1 antagonist is delayed a period of time after administration.

38. The method of claim 35, wherein the drug delivery device is administered two or more times per day.

* * * * *